United States Patent [19]
Krasnov et al.

[11] Patent Number: 6,071,905
[45] Date of Patent: Jun. 6, 2000

[54] BIOLOGICALLY ACTIVE SUBSTANCE ON THE BASIS OF TETRACYCLIC NITROGEN HETEROCYCLES OF PYRIMIDINE ROW

[75] Inventors: Konstantin Andreevich Krasnov, Zheleznovodskaya; Rimma Iliinichna Ashkinazi, Nevsky, both of Russian Federation

[73] Assignee: Natural Drug Sciences, LLC, Ramsey, N.J.

[21] Appl. No.: 09/043,385
[22] PCT Filed: Apr. 2, 1997
[86] PCT No.: PCT/RU97/00098
§ 371 Date: Mar. 17, 1998
§ 102(e) Date: Mar. 17, 1998
[87] PCT Pub. No.: WO98/43982
PCT Pub. Date: Aug. 10, 1998

[51] Int. Cl.[7] .................. A61K 31/549; C07D 513/14
[52] U.S. Cl. ............................ 514/224.5; 544/14
[58] Field of Search ............................ 544/14; 514/224.5

[56] References Cited

U.S. PATENT DOCUMENTS 4,297,355  10/1981  Schering .................. 514/230.8

FOREIGN PATENT DOCUMENTS

| 0409223 | 1/1991 | European Pat. Off. . |
| 2234508 | 6/1991 | United Kingdom . |
| WO 93/12120 | 6/1993 | WIPO . |

*Primary Examiner*—Richard L. Raymond
*Attorney, Agent, or Firm*—Gibbons, Del Deo, Dolan, Griffinger & Vecchione

[57] ABSTRACT

Biologically active substance on the basis of tetracyclicnitrogen heterocycles of pyrimidine row for treating tuberculosis, mycobacteriousis, viral diseases, infections caused by chlamydias, and also diseases which are accompanied by immunodeficiency, in particular malignant neoplasm, has high antimicrobial activity, in particular to strains of mycobacteria which are resistant to the prototype-isoniazid, and simultaneously possess antiviral activity (relative to herpes simplex viruses), antichylamidial activity and also stimulate production of endogenic interferons in organisms.

It represents a derivative of 5-oxo-5H-[1]-benzopyrano-[5,6-b]-4-oxo-4H-[1,2]-pyrimido-1,4,5,6-tetrahydro-1,3-thiazine (1) of general formula(1).

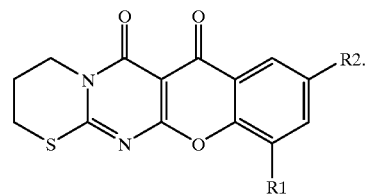

(I–X) where: R1-H or halogen; R2-H, or halogen, or nitro-group, or hydroxy-group or methoxy-group.

13 Claims, No Drawings

BIOLOGICALLY ACTIVE SUBSTANCE ON THE BASIS OF TETRACYCLIC NITROGEN HETEROCYCLES OF PYRIMIDINE ROW

The present application is a 371 of PCT/RU97/00098, filed Apr. 2, 1997.

BACKGROUND OF THE INVENTION

The present invention relates to medicine, and more specifically to pharmacology, veterinary, cosmetology, and in particular to synthetic biological active compound of heterocycle series, which possess antimicrobial, antiviral, antichlamydia and immune stimulating activities: derivatives of 5-oxo-5H-[1]-benzopyrano-[5,6-b]-4-oxo-4H-[1,2]-pyrimido-1,4,5,6-tetrahydro-1,3-thiazine. The derivatives mentioned above have high antimicrobial activity to various mycobacteria, substantial antiviral activity relative to Herpes simplex virus, high antichlamydial activity, and also activity as inducers of interferon. The substances compounds are intended, mainly, for the use in medical practice for treating tuberculosis, mycobacteriosis, viral diseases, infections caused by chlamydia, and also diseases which are accompanied by immunodeficiency, in particular malignant neoplasm. In addition, the above mentioned compound can be used for the same purposes in veterinary and cosmetology.

As known, there are many unsolved problems in modern chemotherapy of infectious diseases. Among bacterial infections one of the most serious problems is caused by tuberculosis, whose treatment is especially complicated due to high resistivity of tuberculosis mycobacteria to the action of chemotherapeutical agents [1]. Moreover, existing compounds possess substantial disadvantage-wide spread of mycobacteria which are resistant to them.

Historically first antituberculosis compounds were derivatives of phenols, benzioc acids (2), mercaptobenzimidizols (3), p-aminosalicyclic acid (4). The most active antituberculosis agents were derivatives of isonicotine acid discovered at the end of $40^s$ of our century, such as isoniazide and its analogs, which are used at present, ethionamide, ethambutole, aminoglycosides, rifampicin, fluoroquinols (1). During therapy of tuberculosis and mycobateriosis usually 2–3 compounds are simultaneously prescribed, which slow appearance of resistant forms of mycobacteria, but do not solve the problems of getting used and resistance completely. Therefore search for new active antituberculosis agents, including those which act on forms of mycobacteria which are resistant to isoniazide, is still actual. Viral diseases pose for modern medicine problems which are not less serious. As a rule, viral infections, such as those caused by viruses of herpes group, are very difficult to be treated, which is connected with insufficient efficiency of existing compounds as well as fast changes of viruses, whose mutations cause appearance of resistant forms (5–7). Synthetic compounds for treatment of diseases caused by viruses of herpes group include acylovir, gancyclovir, retrovir (5) and others whose efficiency is not always sufficient.

Many problems exist during treatment of diseases caused by chlamydia, including widely spread urogenital infections (8). Chlamydia of which are intracellular parasites, are little accessible for the majority of existing compounds and, in addition to this, widespread resistance to the latter caused an appearance of a great number of chronic forms of diseases. To treat chlamydia infections, usually there are used compounds of tetracycline series, macrolids and fluoroquinolones, for example ciprophoxacin (8).

Frequently diseases of viral and bacterial nature occur on the background of reduction of activity of organism immune system, and therefore the problem of development of efficient compounds for treatment of immune deficient states of various origin is also one of the most actual problems. In addition, stimulation of activity of immune system contributes to fight of organism against tumoral processes during which multiple resistance to existing treatment compounds is observed (9).

It is necessary to note that at present intense search of biologically active compounds among derivatives of pyrimidine series is conducted. In particular, in the pyrimidine series a lot of derivatives are known which are used as medicinal compounds (10). Monocyclic derivatives of pyrimidine, in particular barbituric acids possess universal antibacterial action because of antagonism with pyrimidine basis of DNA (11). Active bactericidal compounds are found between hydrazine derivatives of pyrimidine, thyopyrimidines (14), alkoxy-and aminopyrimidines (15). Ethers of pyrimidinecarboxylic acids exhibit antitumor activity (16). Many derivatives of barbituric acids possess substantial antiviral activity (13,17). Derivatives [4,2-b] of pyrimidopyran possess anti-inflammatory properties (18). The same action is found in many N-aryl and N-cyclohexyl-barbituric acid (19). All examples presented hereinabove are united by common chemical structure, since they are monocyclic derivatives of pyrimidine (containing one pyrimidine heterocycle, not conjugated with other cycling systems).

An example of finding biological properties in three cyclic derivatives of pyrimidine row is known, but their action is limited by anti-allergic activity (20) and is not extended to the area of antimicrobial and antiviral action. Derivatives of 2,4-[1H, 3H, 5H]-[1] benzopyrano [2,3-d]-pyrimidine patented as anti-allergic agents are the closest to the claimed compounds as to chemical structure (20).

As a prototype, there is selected hydrazide of izonicotinic acid (isoniazide) (9). The selection is based on its coincidence with the claimed substance as to important objective: anti-tuberculosis action. Izoniazide is one of the most efficient anti-tuberculosis compounds, it can be used in any medicinal forms (pills, injections, inhalations), and at the same time the object of the invention and the prototype belong to the class of nitrogen heterocycles as to their chemical structure.

OBJECTIVE OF THE INVENTION

Objective of the invention is to obtain new chemical compounds which have high antimicrobial activity, in particular to strains of mycobacteria which are resistant to the prototype-isoniazide, and simultaneously possess antiviral activity (relative to herpes simple viruses), antichlamydial activity and also stimulate production of endogenic interferons in organisms. In other words, the objective of the invention is a chemical synthesis of biologically active substances which are superior to the prototype not only in a range of action on strains of tuberculosis and other mycobacteria, but also possess antiviral, antichlamydial and immunostimulating action.

DESCRIPTION OF PREFERRED EMBODIMENTS

The proposed objection is solved by synthesis of a new class of heterocyclic compound compounds-5-oxo-5H-[1]-benzopyrano [5,6-b]4-oxo-4H-[1,2]-pyrimido-1,4,5,6-tetrahydro-1,3-thiazine (1) derivatives of general formula (1)

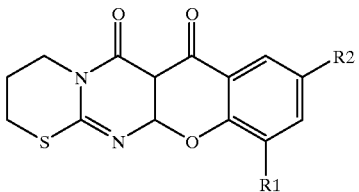

(I–X), where: R1=H, or halogen; R2=H, or halogen, or nitro group, or hydroxy group, or methoxy group.

The proposed objective can be resolved at R1=R2=H (I); R1=H and R2=Cl (II); R1=R2=Cl (III); R1=H and R2=Br (IV); R1=R2=Br (V); R1=H and R2=NO$_2$ (VI); R1=Cl and R2=NO$_2$ (VII); R1=Br and R2=NO$_2$ (VIII); R1-H and R2=OCH$_3$ (IX); R1=H and R2=OH (X).

The claimed compounds are new since they are not known from available sources of information.

The claimed solution is not obvious. As known, practically it is not possible to predict in advance biological activity of new condensed heterocyclic systems. Therefore, to obtain a group of claimed compounds which are complicated tetracyclic structures with four heteroatoms (two atoms of nitrogen, one atom of oxygen and one atom of sulfur) and to find their antimicrobal immunostimulating and antiviral properties is not derived in an obvious manner from the modern state of art.

DISCLOSURE OF INVENTION

The synthesis of the claimed substances proposed by us includes two main stages:
1. 4-oxo-4H-6-oxy-[1,2-d]-pyrimido-1,4,5,6-tetrahydro-1,3-thiazine (XI) is synthesized from 2-thiobarbituric acid (XII) and 1,3-dihalogenopropane (XIII).
2. A target compounds (I–X) is produced from the intermediate substance (XI) obtained in the first stage and corresponding derivative of salicylaldehyde (XIV). The method is common for all members of the group.

The subject matter of the present invention is explained by two examples of synthesis of the intermediate substance and three examples of synthesis of claimed substances, two tables of yield of intermediate and target products, two tables of characteristics of target products and data of seven experiments for determination of their biological properties presented hereinbelow, where:

Examples 1 and 2 are concrete variants of execution of the first stage of synthesis of the target substance (producing of intermediate substance (XI) or in other words 4-oxo-4H-6-oxy-[1,2-d]-pyrimido-1,4,5,6-tetrahydro-1,3-thiazine, and Example 2 contains generalized multiple variant;

Examples 3, 4, and 5 are concrete variants of execution of second stage of synthesis of claimed substances (production of target products (I–X), or in other words derivatives 5-oxo-5H-[1]-benzopyrano-[5,6-b]-4-oxo-4H-[1,2]-pyrimido-1,4,5,6-tetrahydro-1,3-thiazine.

Table 1 contains the date of yield of intermediate substance(XI), or in other words 4-oxo-4H-6-oxy-[1,2-d]-pyrimido-1,4,5,6-tetrahydro-1,3-thiazine.

Table 2 shows methods of synthesis and contains data of yield of target products (I–X), synthesed by different methods or in other words derivatives 5-oxo-5H-[1]-benzopyrano-[5,6-b]-4-oxo-4H-[1,2]-pyrimido-1,4,5,6-tetrahydro-1,3-thiazine.

Table 3 contains the melting points constants and data of NMR $^1$H spectra of target products (I–X), or in other words derivatives 5-oxo-5H-[1]-benzopyrano-[5,6-b]-4-oxo-4H-[1,2]-pyrimido-1,4,5,6-tetrahydro-1,3-thiazine.

Table 4 shows data of elementary analysis of target products(I–X), or in other words derivatives 5-oxo-5H-[1]-benzopyrano-[5,6-b]-4-oxo-4H-[1,2]-pyrimido-1,4,5,6-tetrahydro-1,3-thiazine.

Data of 7 series of experiments for determination of biological activity of claimed compounds contain:

Experiment 1—determination of antimicrobial action;

Experiment 2—determination of action of claimed compounds on pathogenic mycobacteria;

Experiment 3—determination of acute toxicity;

Experiment 4—therapeutic efficiency during experimental tuberculosis;

Experiment 5—determination of action on herpes virus;

Experiment 6—determination of interferon-inducing activities.

Experiment 7—determination of action on C.trachomatis.

EXAMPLE 1

Variant of execution of the first stage of synthesis of claimed compounds (producing of intermediate (XI), or in other words 4-oxo-4H-6-oxy-[1,2-d]-pyrimido 1,4,5,6-tetrahydro-1,3-thiazine) (XI)

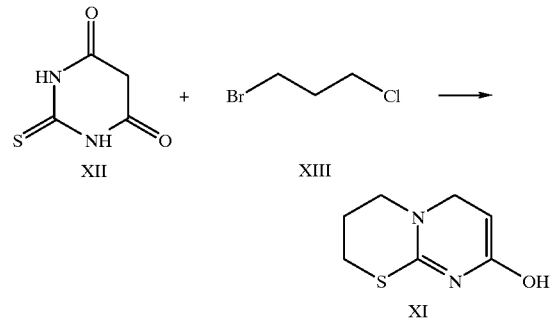

14.4 g (0.1 mol) 2-thiobarbituric acid (XII) is added to 100–150 ml of water-alcohol solution of 0.2 mol alkali and mixed. Then 0.1 mol of 1-bromo-3-chloropropane (XIII) is added, and the mixture is mixed with heating. In the process of reaction pH of the solution is reduced. After the end of reaction the solution is cooled, the precipitated residue is separated and washed. For purifying, the product is dissolved in aqueous alkali and precipitated byhydrochloric acid. Yield of 4-oxo-4H-6-oxy-[1,2-d]-pyrimido-1,4,5,6-tetrahydro-1,3-thiazine is 9.7 g (43.8%), melting point 250–260° C. (with deviation).

It is found, %: C 45.02; H 5.27; N 14.09; S 17.1 1; ($C_7H_8N_2O_2S$).

Calculated, %: C 45.07; H 5.21; N 14.15; S 17.02 NMR $^1$H spectrum, (DMSO-d6, δ, δ ppm): 2.18, m (2H, CH$_2$); 3.19 t (2H, SCH$_2$); 3.90 t(2H, NCH$_2$); 5.08 s (1H, CH); 11.06 s(1 H, OH).

EXAMPLE 2

Variant of execution of the first stage of synthesis of claimed compounds (producing of intermediate XI, or in other words 4-oxo-4H-6-oxy-[1,2-d]-pyrimido-1,4,5,6-tetrahydro-1,3-thiazine) (XI).

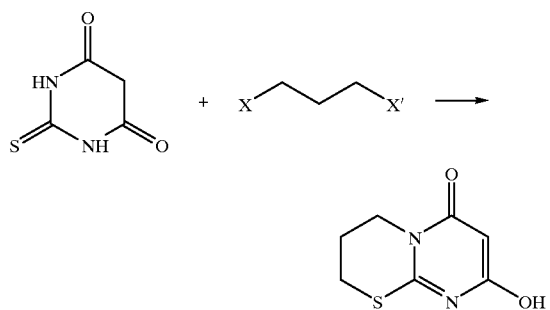

Alkylation of 2-thiobarbituric acid (XII) is performed by 1.3 dihalogenoderivatives of propane of general formula X—CH$_2$—CH$_2$—CH$_2$—X'(XIII) (where X,X'—Cl, Br or J). The process is performed analogously to Example 1. Yields of the product are presented hereinbelow.

TABLE 1

Yields of Intermediate Substance (XI) in Dependence on Nature of Haloid In Molecule of Reactant (XIII) and Concentration of Alcohol in Reaction Solution

| X | X' | Concentration of alcohol, % | Yield of product (XI), % |
|---|----|-----------------------------|--------------------------|
| Cl | Cl | 50 | 11.5 |
| Br | Br | 50 | 46.1 |
| Br | I  | 50 | 47.0 |
| I  | I  | 50 | 42.5 |
| Cl | Br | 50 | 43.8 |
| Cl | Br | 20 | 33.4 |
| Cl | Br | 80 | 39.6 |

EXAMPLE 3

Variant of execution of the second stage of synthesis of the claimed substance (producing of target product, in particular 5-oxo-5H-[1]-benzopyrano-[5. 6-b]-4-oxo-4H-[1,2]-pyrimido-1,4,5,6-tetrahydro-1,3-thiazine (1).

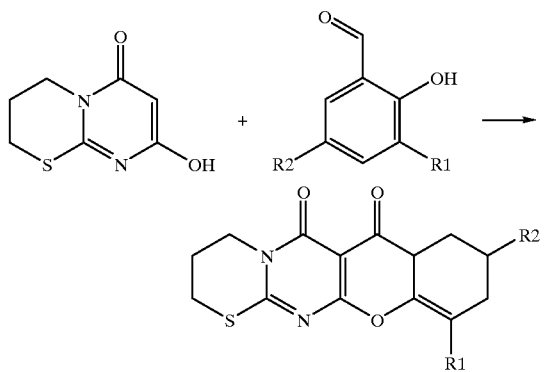

Mixture 1.84 g (0.01 mol) 4-oxo-4H-6-oxy-[1,2-d]-pyrimido-1,4,5,6-tetrahydro-1.3-thiazine (XI) and 1.83 g (0.015 mol) of salicylaldehyde (XV),(R1=R2=H) is heated, till evaporation of water vapors formed during the reaction is stopped. Then the formed reaction mass is thoroughly washed with alcohol for removing initial and side products, and the residue is recrystalized from acetic acid to obtain the target product-5-oxo-5H-[1]-benzopyrano-[5,6-b]-4-oxo-4H-[1,2]-pyrimido-1,4,5,6-tetrahydro-1,3-thiazine. The yield is given Table 2, and the characteristics in the Table 3, while data of elementary analysis are given in the Table 4.

EXAMPLE 4

Variant of execution of second stage of synthesis of claimed substances (production of target product, in particular 3-chloro-5-oxo-5H-[1]-benzopyrano-[5,6-b]-4-oxo-4H-[1,2]-pyrimido-1,4,5,6-tetrahydro-1,3-thiazine (II).

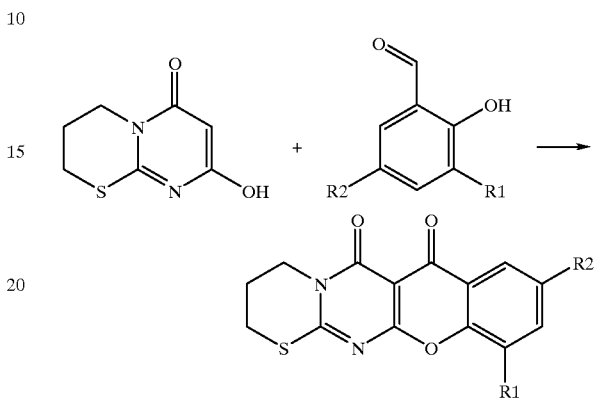

(R1=H, R2=Cl) (R1=H, R2=Cl) Mixture 1.84 g (0.01 mol) 4-oxo-4H-6-oxy-[1,2-d]-pyrimido-1,4,5,6-tetrahydro-1,3-thiazine (XI) and 2.35 g (0.015 mol)-5-clorosalicylaldehyde (XV), (R1=H, R2=Cl) in highly boiling inert solvent (chlorobenzene, anizole, diglim, diethyleneglycol, is heated to disappearance of initial pyrimidothiazine. After this the sediment is separated, thoroughly washed and dried. The target product obtained is 3-chloro-5-oxo-5H-[1]-benzopyrano-[5,6-b]-4-oxo-4H-[1,2]-pyrimido-1,4,5,6-tetrahydro-1,3-thiazine. The yield is given in the Table 2 and the characteristics are given in the Table 3, while the data of element analysis are given in the Table 4.

EXAMPLE 5

Variant of execution of the second stage of synthesis of claimed compound (producing of target product, in particular 1,3-dichloro-5-oxo-5H-[1]-benzopyrano-[5,6-b]-4-oxo-4H-[1,2]-pyrimido-1,4,5,6-tetrahydro-1,3-thiazine (III).

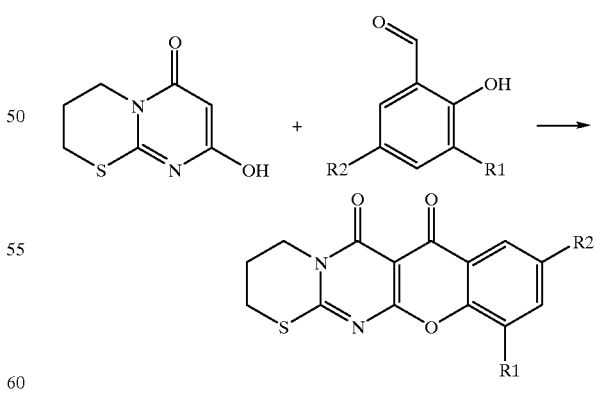

Mixture of 1,84 g (0.01 mol) 4-oxo-4H-6-oxy-[1,2-d]-pyrimido-1,4,5,6-tetrahydro-1.3-thiazine (XI) and 1.83 g (0.015 mol) of dichlorosalicylaldehyde (XV), (R1=R2=Cl), is boiled in ethanol for 6–8 hours. The produced sediment is filtered out, washed with hot ethanol and dried. The target product is obtained 1,3-dichloro-5-oxo-5H-[1]- benzopyrano-[5,6-b]-4-oxo-4H-[1,2]-pyramido-1,4,5,6-tetrahydro-1,3-thiazine. Yield is given in the Table 2, characteristics in the Table 3, data of element analysis in the Table 4.

The remaining target compounds-are derivatives 5-oxo-5H-[1]-benzopyrano-[5,6-b]-4-oxo-4H-[1,2]-pyrimido-1,4,5,6-tetrahydro-1,3-thiazine (IV–X), where:

3-bromo-5-oxo-5H-[1]-benzopyrano-[5,6-b]-4-oxo-4H-[1,2]-pyrimido-1,4,5,6-tetrahydro-1,3-thiazine (IV), R1=H, R2=Br;

1,3-dibromo-5-oxo-5H-[1]-benzopyrano-[5,6-b]-4-oxo-4H-[1,2]-pyrimido-1,4,5,6-tetrahydro-1,3-thiazine(V), R1=R2=Br;

3-nitro-5-oxo-5H-[1]-benzopyrano-[5,6-b]-4-oxo-4H-[1,2]-pyrimido-1,4,5,6-tetrahydro-1,3-thiazine (VI), R1=H, R2=NO$_2$;

1-chloro-3-nitro-5-oxo-5H-[1]-benzopyrano-[5,6-b]-4-oxo-4H-[1,2]-pyrimido-1,4,5,6-tetrahydro-1,3-thiazine (VII) R1=Cl, R2=NO$_2$;

1-bromo-3-nitro-5-oxo-5H-[1]-benzopyrano-[5,6-b]-4-oxo-4H-[1,2]-pyrimido-1,4,5,6-tetrahydro-1,3-thiazine (VIII), R1=Br, R2=NO$_2$;

3-methoxy-5-oxo-5H-[1]-benzopyrano-[5,6-b]-4-oxo-4H-[1, 2]-pyrimido-1,4,5,6-tetrahydro-1,3-thiazine (IX), R1=H, R2-OCH$_3$;

3-hydroxy-5-oxo-5H-[1]-benzopyrano-[5,6-b]-4-oxo-4H-[1,2]-pyrimido-1,4,5,6-tetrahydro-1,3-thiazine (X), R1=H, R2=OH are produced from 4-oxo-4H-6-oxy-[1,2-d]-pyrimido-1,4,5,6-tetrahydro-1,3-thiazine (XI) and corresponding salicylaldehyde derivative (XV) in accordance with the Examples 3,4 and 5 presented above. The methods of synthesis and yields of products are given in Table 2, the characteristics in Table 3, the data of element analysis in Table 4.

TABLE 2

Methods of Synthesis and Yield of Target Product (I-X)

| No Compounds | R1 | R2 | Method of synthesis (No of Example) | Yield % |
|---|---|---|---|---|
| I | H | H | 3 | 41.0 |
| I | H | H | 4 | 38.5 |
| I | H | H | 5 | 22.4 |
| II | H | Cl | 3 | 39.9 |
| II | H | Cl | 4 | 40.4 |
| III | Cl | Cl | 3 | 44.6 |
| IV | H | Br | 3 | 42.1 |
| V | Br | Br | 4 | 35.5 |
| VI | H | NO$_2$ | 3 | 31.3 |
| VI | H | NO$_2$ | 4 | 16.2 |
| VI | H | NO$_2$ | 5 | 34.6 |
| VII | Cl | NO$_2$ | 5 | 37.5 |
| VIII | Br | NO$_2$ | 5 | 37.0 |
| IX | H | OCH$_3$ | 3 | 24.7 |
| X | H | OH | 3 | 18.3 |

TABLE 4

Data of Elementary Analysis of Derivatives of 5-oxo-5h-[1]-Benzopyrano-[5,6,-b]-4-oxo-4H-[1,2]-pyrimido-1,4,5,6-tetrahydro-1,3-thiazine (I-X)

| N$^Q$ PRODUCT | Found % | | | | | Brut to | Calculated % | | | | |
|---|---|---|---|---|---|---|---|---|---|---|---|
| | C | H | Cl(Br) | N | S | | C | H | Cl(Br) | N | S |
| I | 58.69 | 3.46 | — | 9.82 | 11.28 | C$_{14}$H$_{10}$N$_2$O$_3$S | 58.74 | 3.49 | — | 9.80 | 11.21 |
| II | 50.86 | 2.94 | 11.00 | 8.60 | 9.98 | C$_{14}$H$_8$ClN$_2$O$_3$S | 51.09 | 2.83 | 11.04 | 8.73 | 10.00 |
| III | 46.99 | 2.24 | 20.05 | 7.77 | 9.01 | C$_{14}$H$_8$Cl$_2$N$_2$O$_3$S | 47.03 | 2.28 | 19.99 | 7.89 | 9.03 |
| IV | 46.06 | 2.45 | 21.82 | 7.61 | 8.73 | C$_{14}$H$_8$BrN$_2$O$_3$S | 46.03 | 2.47 | 21.89 | 7.67 | 8.78 |
| V | 37.80 | 1.84 | 36.11 | 6.30 | 7.24 | C$_{14}$H$_8$Br$_2$N$_2$O$_3$S | 37.84 | 1.82 | 36.00 | 6.31 | 7.22 |
| VI | 50.53 | 2.69 | — | 12.98 | 9.62 | C$_{14}$H$_9$N$_3$O$_5$S | 50.75 | 2.74 | — | 13.00 | 9.66 |
| VII | 45.68 | 2.19 | 9.70 | 11.47 | 8.65 | C$_{14}$H$_8$ClN$_3$O$_5$S | 45.97 | 2.20 | 9.70 | 11.50 | 8.77 |
| VIII | 40.81 | 1.93 | 10.18 | 10.21 | 7.83 | C$_{14}$H$_8$BrN$_3$O$_5$S | 40.99 | 1.96 | 19.50 | 10.24 | 7.82 |
| IX | 56.78 | 3.73 | — | 8.81 | 10.06 | C$_{15}$H$_{12}$N$_2$O$_4$S | 56.96 | 3.80 | — | 8.86 | 10.14 |
| X | 55.77 | 3.28 | — | 9.22 | 10.54 | C$_{14}$H$_{10}$N$_2$O$_4$S | 55.63 | 3.31 | — | 9.275 | 10.61 |

TABLE 3

Melting Points and Data of NMR $^1$H Spectra of 5-oxo-5H-[1]-benzopyrano-[5,6-b]-4-oxo-4H-[1,2]-pyrimido-1,4,5,6-tetrahydro-1,3-thiazine Derivative (I-X)

| No Compound | T Melting Point °C. | Chemical Shift, in ppm | | | | | |
|---|---|---|---|---|---|---|---|
| | | CH$_2$ | CH$_2$S | CH$_2$N | ArH | OCH$_3$(OH) | Solvent |
| I | 299 | 2.25 | 3.28 | 4.01 | 7.34 m(2H); 7.71 t; 8.14 m | — | DMSO-d$_8$ |
| II | 306 | 2.26 | 3.29 | 4.06 | 7.32 m; 7.92 m; 8.28 c | — | DMSO-d$_8$ |
| III | 316 | 2.28 | 3.31 | 4.06 | 7.90 c; 8.11 c | — | DMSO-d$_6$ |
| IV | 319 | 2.29 | 3.28 | 4.08 | 7.39 m; 7.99 m; 8.30 c | — | DMSO-d$_6$ |
| VII | 315 | 2.39 | 3.30 | 4.22 | 8.01 c; 9.18 c | — | CDCl$_3$ |
| VII | 315 | 2.39 | 3.30 | 4.22 | 8.01 c; 9.18 c | — | DMSO-d$_6$ |

TABLE 3-continued

Melting Points and Data of NMR $^1$H Spectra of 5-oxo-5H-[1]-benzopyrano-
[5,6-b]-4-oxo-4H-[1,2]-pyrimido-1,4,5,6-tetrahydro-1,3-thiazine Derivative (I-X)

| No Compound | T Melting Point °C. | CH$_2$ | CH$_2$S | CH$_2$N | ArH Chemical Shift, in ppm | OCH$_3$(OH) | Solvent |
|---|---|---|---|---|---|---|---|
| VIII | 321 | 2.39 | 3.30 | 4.21 | 8.05 c; 9.22 c | — | DMSO-d$_6$ |
| IX | 292 | 2.26 | 3.26 | 4.09 | 7.41 m; 7.99 m; 8.54 c | 3.97 | CDCL$_3$ |
| X | 290 | 2.20 | 3.21 | 4.05 | 7.18 m; 7.92 m; 8.31 c | 9.12 | DMSO-d$_6$ |

Experimental Tests of Biological Activity of Claimed Compounds

Experiment 1

Determination of Antimicrobial Action of Compounds

In order to determine antimicrobial activity standard strains Mycobacterium smegmatis ATCC607 and Mycobacterium tuberculosis H37RV were used which are sensitive to all antimicrobial compounds.

The evaluation of antimicrobial action was performed with the method of series culture (5). M. smegmatis ATCC607 for seeding was grown on liquid synthetic medium N-1.

The compounds were dissolved in dimethyl sulfoxide (DMSO) and tittered in medium N-1, so that this compound was contained in separate test tubes with the medium in concentration of 200–0.025 mg/l. The concentration of the compound in the medium of neighboring test tubes was differed twice. For the control, DMSO which was tittered the same as the compound, was utilized. Test strain of bacteria was added in the quantity 1–2×10$^6$ ml. The result was considered after 72 hour cultivation of test tubes at 37° C.

For M tuberculosis H37Rv conditions of experiment were identical, with the exception of the fact that bacteria were grown on the Soton medium which contains 10% horse serum, and density of microbial suspension during seeding was (5.0×10$^6$) in ml.

As the control, in both cases known tuberculostatic compounds were utilized. The results obtained for the used strains are summarized in Table 5.

TABLE 5

Minimum Inhibitory Concentration (MIC) Relative to
M. tuberculosis H37Rv and M. smegmatis ATCC607 (mg/l)

| | | MIC | |
|---|---|---|---|
| NN | Compound | M. tuberculosis | M. smegmatis |
| 1. | R1=R2=H | 0.6 | 0.3 |
| 2. | R1=H, R2=Cl | 10.0 | 10.0 |
| 3. | R1=R2=Cl | 0.3 | 1.0 |
| 4. | R1=H, R2=Br | 25.0 | 50.0 |
| 5. | R1=R2=Br | 0.1 | 0.1 |
| 6. | R1=H, R2=NO$_2$ | 50.0 | 100.0 |
| 7. | R1=Cl, R2=NO$_2$ | 50.0 | 100.0 |
| 8. | R1=Br, R2-NO$_2$ | 25.0 | 100.0 |
| 9. | R1=H, R2=OCH$_3$ | 50.0 | 100.0 |

TABLE 5-continued

Minimum Inhibitory Concentration (MIC) Relative to
M. tuberculosis H37Rv and M. smegmatis ATCC607 (mg/l)

| | | MIC | |
|---|---|---|---|
| NN | Compound | M. tuberculosis | M. smegmatis |
| 10. | R1=H, R2=OH | 50.0 | 100.0 |
| Controls | | | |
| 1. | Streptomycin | 0.2 | 0.15 |
| 2. | Isoniazid | 0.1 | 1.5 |
| 3. | Rifamycin | 0.05 | 0.25 |
| 4. | Ethambutol | 5.0 | 5.0 |
| 5. | Ofloxacin | 0.5 | 0.5 |

The claimed compounds possess antibacterial activity relative to the used strains of mycobacteria in concentrations of 100.0–0.1 mg/l. The activity of action on mycobacteria of series of claimed compounds in vitro is not less, and sometimes more than that of known antituberculosis compounds.

Experiment 2

Determination of Action of Compounds of Pathogenic Mycobacteria

In this work strains taken from patients in clinics of St. Petersburg (Russia) in 1996 were utilized: M. tuberculosis 61 (S)— which is sensitive to action of known antimicrobial compounds (aminoglycosides, rimfamycin, isoniazid, ethambutol); M. tuberculosis 16(R)— which is resistant to basic antimicrobial compounds; Mycobacterium avium 84-mycobacteria which causes a sickness and death of persons, infected with Human Immunodeficiency Virus (HIV). The test were conducted on the Lowenstein-Jensen medium. The compounds dissolved in DMSO were added to separate test tubes with the medium in final concentration 10 mg/l. After seeding of tests strains on the surface of the medium, the test tubes were incubated during 30 days. In the control, DMSO were used in corresponding concentration as well as standard compounds used for treatment of tuberculosis and mycobacteriosis (Table 6).

TABLE 6

Spectrum of Antimicrobial Action of Claimed Compounds Relative to Various Mycobacteria, Obtained from Patients (Concentration of Compound 10.0 g/l).

| Number | Compound | M. tuberculosis 61S* | M. tuberculosis 16R** | M. avium 84 |
|---|---|---|---|---|
| 1. | R1=R2—H | complete growth inhibition | complete growth inhibition | complete growth inhibition |
| 2. | R=R2=Cl | complete growth inhibition | complete growth inhibition | complete growth inhibition |
| 3. | R1=R2=Br | complete growth inhibition | complete growth inhibition | complete growth inhibition |
| Control | | | | |
| 1. | Streptomicyn | complete growth inhibition | growth | growth |
| 2. | Isioniazid | complete growth inhibition | growth | growth |
| 3. | Rifamycin | complete growth inhibition | growth | growth |
| 4. | Ethambutol | complete growth inhibition | growth | partial growth inhibition |

*-sensitive to control compounds
**-resistant to control compounds

Obtained data show that the claimed compounds presented in Table 6 inhibit the growth of all types and strains of mycobacteria used in the test. Therefore, in vitro they act on the strain of mycobacteria obtained from patients which are resistant to main compounds used for treatment of tuberculosis. Moreover, these compounds in the given conditions inhibit the growth of M. avium. The remaining claimed compounds posses lower antimicrobial activity in analogous conditions.

Experiment 3

Determination of Acute Toxicity

Determination of acute toxicity was performed on no-breed white mice with mass 18–20 g. Emulsions of claimed compounds were introduced in various concentrations: 1500, 700, 500, 100, 20 and 5 mg/kg. Five animals were used to test each concentration of the compound. The compound was introduced once a day through orally or intraperitoneal. The period of observation was 14 days. On 1,8 and 15 day weighing of animals of each group was performed. For the control, animals were utilized, in which the emulsion prepared without tested compounds was introduced.

For microscopic investigation of internal organs, dissection of all animals which died during test and which survived at the end of the tests was carried out.

During the investigation no weight loss, changes in behavior and external appearance as well as animal death were observed. Based on the results of the dissection, no microscopical pathology of the internal organs of animals in the test group and the control groups were found (Table 7).

TABLE 7

Acute Toxisity of (LD 50) of Tested Compounds (mg/kg)

| NN | Compound | LD 50 |
|---|---|---|
| 1. | R1=R2=H | >1500 |
| 2. | R1=R2=Cl | >1500 |
| 3. | R1=R2=Br | >1500 |

The obtained results prove that with oral and intraperitoneal intake the claimed compound in concentration 1500 mg/kg do not have acute toxicity for mice.

Experiment 4

Therapeutic Efficiency of Action of Claimed Compounds During Experimental Tuberculosis Process in Mice Investigation was conducted on no-breed male mice with mass18–20 g. Tuberculosis process was caused in mice by introduction into a tail vein of M. bovis bovinus 8 in the dose of 0.1 mg/mouse as a bacterial suspension (0.2 ml). The tested compounds were used in three dosages(10, 20 and 30 mg/kg). Streptomycin was used as a compound for comparison. The tested compounds were introduced into animals once a day orally and streptomycin was introduced intramuscularly. Withdrawal of animals from the test (by decapitation) was executed at 42 day after infection, when in the control infection group (not treated mice) 45% of animals perished.

Efficiency of the therapy was evaluated in accordance with: survival of animals, relative mass of lungs, index of damage of lungs and seeding of mycobacteria from spleen. In the latter case, homogenate of the organ was seeded on dense egg medium of Levenshtein-lensen. Count of colonies was performed 25–30 days after cultivation. Average seeding of mycobacteria on one sample was counted, which was presented as a number of colony forming units (CFU) per 100 mg (Table 8).

TABLE 8

Evaluation of Efficiency of Action of Tested Compounds on Infection Caused in Experimental Animals

| Animal Group | Perished animals | Coefficient of lung mass(con. units) | Index of damage lungs(con. unit) | SeedingM.tu b.(CFU) |
|---|---|---|---|---|
| Control group | 45% | 3.24 | 4.5 | 300 |
| Streptomycin | 0 | 2.47 | 2.45 | 200 |
| R1=R2=Cl | 0 | 2.42 | 2.5 | 195 |
| R1=R2=Br | 0 | 2.30 | 2.3 | 180 |

CFU—are colony forming units

The conducted investigations show that in experimental animals with generalized tuberculosis process, the claimed compound compounds showed therapeutical effect, which as to the exhibited activity, is not less than that of streptomycin.

Experiment 5

Determination of Action of Claimed Compounds on Herpes Virus

Antiviral activity was studied relative to the herpes virus I of the type (VPG-1/Leningrad/248/88) in accordance with a well known method(21).

The viruses were grown on inoculated culture of cells Vero, obtained from the bank of cellular cultures of Institute of Cytology RAS.

The procedure of the experiment.

To cells which were grown on the medium RPMI-1640 with 10% bovine serum and introduced into wells of 96-wells plate, virus in a final concentration 10 part/ml and the claimed compounds diluted in DMSO with final concentration 100, 10 and 1 mg/l were added. For each tested concentration of the compound 5 independent holes were used. The plate was incubated during 60 min at 38° C. in $CO_2$-incubator. After the incubation the virus was withdrawn and again fresh medium was introduced containing the claimed compounds in used concentrations.

The results were evaluated as to the presence of cytopathogenic action of virus on the cells after 36 hours of incubation at 38° C. in $CO_2$ incubator.

The following controls were used in the experiment.
1. Control of cell culture (ability to normal growth).
2. Control of virus (evaluation of ability to reproduction).
3. Control of antiviral activity of antiviral compound acyclovir
4. Control of compounds (toxicity of compounds).
5. Control of solvent (DMSO) as to toxicity.

For evaluation of cytopathic action of virus, the number of unchanged cells in 100 fields formed by a special net of an eye piece of an inverted microscope was calculated. The obtained results are presented in Table 9.

TABLE 9

Action of Claimed Compounds to Herpes of Simplex Virus

| NN | Compound | Concentration of Tested Compounds(mg/l) | | |
|---|---|---|---|---|
| | | 100 | 50 | 10 |
| 1. | Acyclovir | —* | — | 8000**(80%)*** |
| 2. | DMSO | 10000 | 10000 | 10000 |
| 3. | R1=H R2=$NO_2$ | toxic | toxic | 6000 (60%) |
| 4. | R1=R2=$NO_2$ | toxic | 5000 (50%) | 4000 (40%) |
| 5. | R1=R2=H | toxic | 6000 (60%) | 3000 (30%) |
| 6. | Control of Cells | 10000 | 10000 | 10000 |

*— compound of given concentration which is not tested
**number of cells in 100 fields under consideration
***—in the brackets the percentage of protection of cells from virus when compared with the control of cell cultures is presented.

The obtained results show that the claimed compound presented in Table 9 possess antiherpes activity which is comparable with that of a standard compound acyclovir.

The remaining claimed compounds had less pronounced activity in the process of suppression of reproduction of herpes virus in the selected conditions of experiment.

Experiment 6

Determination of Interferon-inducing Activity of Claimed Compounds

Induction of the synthesis of interferons with the claimed compounds was performed on the primary culture of human lymphocytes (in particular these cells in the human organism are main producers of interferons). In order to obtain the culture of lymphocytes, fresh (12 hours after taking) blood of healthy donors (not of second group) was used. In order to separate lymphocytes, heparin-treated blood obtained from a healthy donor was subjected to centrifuging in a gradient of density ficoll-verographin 1.71 $g/cm^3$ for separation of fraction of immuno-competent cells. This fraction was selected and reproduced by a nutrient medium RPMI-1640 containing 5% of Fetal calf serum, 0.3 mg/ml of L-glutamine, 100 unit/ml of penicillin 50 g/ml of streptomycin. Concentration of lymfocytes was considered after covering with Methylene Blue and counting of the number of cells in the Goraev chamber. The initial solvents of the claimed substances were diluted by the nutrient medium RPMI-1640 so that the final concentration of substances will form a row: 100 mg/l, 10 mg/l, 1 mg/l after introduction of lymphocyte suspension. The final concentration of lymphocytes in the induction mixture was $3 \times 10^6$ cell/ml. Parallel to the test samples the following controls were presented:
1) Control of spontaneous production of interferons (IFN) by lymphocytes;
2) Control of process flow under the action of standard IFN inductor N-metyl-N-(α, D-glucopyranosyl)-ammonium-10-methylene carboxylateacrydone (cycloferon).
3) Control of process flow under the action of standard IFN Neovir(sodium 10-methylenecarboxylate-9-acrydone) with corresponding content of DMSO in test samples.
4) Control of spontaneous production of interferons in the presence of DMSO, in the quantity corresponding to tested samples.

Control and test samples were incubated for 24 hours at 37° C. After the incubation the samples were centrifuged at 2000 G for sedimentation of cellular elements, and from the samples IFN-containing supernatant was withdrawn, which was analyzed as to quantitative content of IFN. The sediment of the cells was resuspended in the former volume of nutrient medium, colored with vital coloring-tripan Blue, and the number of cells was counted in the Goriaev chamber (as described hereinabove) for determination of cytotoxic action of the compounds.

The quantitative determination of IFN content in control and test samples was performed with the use immunoferment test system for IFN produced by TOO "protein contour" Pro Con If2 plus. In order to determine the quantity of interferon in the sample solid-phase immunoferment method was used with the utilization of Peroxidase of horse radish as an indicator ferment. Activity of bonded peroxides was measured with the use of automatic photometer for microplates with a microprocessor at the wave length of 450 nm.

For counting the results, the activity of IFN in standard solutions of IFN containing the known quantity of compound was determined at the same time. Based on the obtained results, a calibrating curve was formed, which permits with the use of the microprocessor of automatic photometer, to obtain data expressed in international units of activity (IU). The results of analysis are expressed in IU activity of IFN per ml in the given induction system which contains $3 \times 10^6$ of lymphocytes in ml. Each test and control point was investigated in four parallels.

Controls of immunoferment reaction.
1. Control DMSO with a nutrient medium.
2. Control of system components (in accordance with instruction).
3. All results were considered only when there was a correspondence of the controls to the passport data of the system.

The obtained results were subjected to statistic analysis in accordance with t-cryterium and calculation of confident interval at p=0.05. The analysis of coincidence of results in the parallel tests was performed. As a result of the performed investigations, it was determined that among the claimed compounds there are samples which have the capability of inducing the synthesis of IFN (Table 10).

TABLE 10

Quantitative Evaluation of IFN Inducing Activity of Claimed Compounds

| N | Compound | Content of IFN in induction mixture after 24 hours of incubation at various concentration of compounds, ($\mu$g/ml), ME/$3*10^4$limph./ml | | |
|---|---|---|---|---|
| | | 100 | 10 | 1 |
| 1. | Control of Limphocytes | 0 | 0 | 0 |
| 2. | Cycloferon | 58 ± 1.4 | 22 ± 2.5 | 3.8 ± 0.8 |
| 3. | Neovir | 66 ± 1.4 | 24.5 ± 1.2 | 4.1 ± 0.5 |
| 4. | Poly I/ poly C | —* | 43.6 ± 2.0 | 10.5 ± 0.8 |
| 5. | DMSO | 0 | 0 | 0 |
| 6. | R1=H, R2=$NO_2$ | 48 ± 1.2 | 20 ± 1.2 | 4.2 ± 0.8 |
| 7. | R1=Cl, R2=$NO_2$ | 36 ± 1.4 | 18 ± 1.6 | 3.6 ± 0.5 |
| 8. | R1=H, R2=Br | 192 ± 1.6 | 84 ± 2.5 | 14 ± 0.5 |
| 9. | R1=R2=Br | 47 ± 0.8 | 23 ± 1.0 | 4.0 ± 0.5 |

*—is a compound of given concentration which was not tested

Experiment 7

Determination of Action of Claimed Compounds to Chlamydia Trachomatis

Antimicrobial activity of claimed compounds was studied relative to C. trachomatis D323—which is a standard strain from collection of the chair of microbiology of S. Petersburg State Pavlov Medical University. This strain was derived from a patient with Chlamydia urethritis and has a morphology and physiological activity which is characteristic for the representatives of this type, it is sensitive to action of compounds used for treatment of a chlamydia infection.

Cell cultures McCoy and L929 obtained from the Institute of cytology of RAS were used in this work.

Procedure of Experiment

Cells were grown in flasks from neutral glass in the medium RPMI-1640 with the addition of 10% of Fetal bovine serum. The test was performed in glass (non toxicity) flat-bottom flasks with cover glasses. The cells were introduced into the medium in the final concentration 1×10 cell/ml. After obtaining of monolayer, in the test tubes, standard infectious dosages of chlamydia which were stored in frozen condition at −70° C. were introduced. Simultaneously, compounds in the final concentration 100 mg/l were added to the cells. The sample was centrifuged at 2400 g during 60 minutes at room temperature and incubated at 37° C. for 2 hours. After this, the nutrient medium was exchanged for a new one, containing 5% embryo bovine serum and cycloheximid (2 mkg/ml) with a repeated introduction of the claimed compounds in the same concentration. Parallel, the samples were doubled with the use of the medium without cycloheximid so as to exclude its action on the investigated substances. The samples were incubated for 48 hours in $CO_2$ incubator.

The controls included: control of cell cultures, control of action of solvents, control of action of chlamydia in the absence of any compounds, control of sensitivity of chlamydia to standard antimicrobial compound ciprofloxacin (19), control of tested compounds as to toxicity relative to cell cultures.

The evaluation of results was performed by determination of chlamydia cytoplasmatic inclusions by means of the method of immunofluorescence (MicroTrac Chlamydia trachomatis Direct Specimen Test) and chlamydia antigens by means of CylaMonoScreen (Russian-British Joint Venture 66 Regent's Parc Road London NW17SX) (22, 23). The effect of action of compound was determined by analysis of the condition of the monolayer and number of cells with CPV relative to the control (cell culture infected with C. trachomatis D323), and there was considered the number of normal cells in 100 vision fields, obtained with the use of special net of eye piece of a microscope.

The results of control samples which satisfied the requirements of the experiment: control of cell culture-morphology of cells and condition of monolayer correspond to the given type of cells, control of chlamydia growth in the cell culture-presence of CPV in the monolayer, control of action of standard antimicrobial compound determination of the reduction of numbers of CPV in the mono layer when compared with the proceeding control. Control of toxicity of claimed compounds toxicity is absent, control of action of solvents-toxic action on the cells is absent. The results of performed tests are presented in Table 11.

TABLE 11

Action of Claimed Substances on *C. trachomatis*

| N | Substance | Number of unchanged cells |
|---|---|---|
| 1. | Cell control | 8.000 |
| 2. | DMSO | 8.000 |
| 3. | Control of infected cells | 6.000 |
| 4. | Ciprofloxacine (100)* | 7.000 (50%)** |
| 5. | R1=H, R2=Br (100) | 7.000 (50%) |
| 6. | R1=H, R2=H (10) | 7.200 (60%) |

*concentration of compound in mg/l is given in brackets
**percent of protection of cells from infection is given in brackets.

The obtained data proved that the claimed compounds presented in Table 11 possess pronounced activity against chlamydia, which exceeds that of a standard compound ciprofloxacine.

The remaining claimed compounds have less pronounced activity as to protection of cells from chlamydia in the given conditions of experiment.

Industrial Applicability

Examples 1–5 and results of practical synthesis and analysis of claimed compounds presented in the Tables 1–4 prove the possibility of laboratory and industrial synthesis of all 10 claimed compound by means managed with modern pharmaceutical industry, and also their clear identification by widely used control methods.

The series of experiments for determination of biological activity presented in seven reports showed that the claimed compounds possess biological activity to various microorganisms including mycobacteria (sensitive and stable to existing compounds) chlamydia, Herpes Simplex viruses and also interferon-inducing activity. The latter indicates the possibility of their use for treatment of some cancer diseases.

The presented facts show the achievement of the objectives posed by the invention: new class of heterocyclic compoundcompounds was synthesized, which possess high and broad biological activity and particular antimycobacteria (causing tuberculosis and mycobacteriosis), immunostimulating, antichlaymidal and antiviral activity.

Therefore, in accordance with our opinion, the claimed agents (compounds) satisfy all requirements for an invention: they are new, unobvious, and industrially applicable.

What is claimed is:

1. A biologically active substance characterized in that it represents a derivative of 5-oxo-5H-[1]-benzopyrano-[5,6-b]-4-oxo-4H-[1,2]-pyrimido-1,4,5,6-tetrahydro-1,3-thiazine (1) of the general formula:

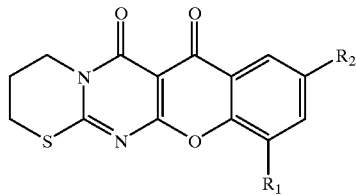

where $R_1$=H, or a halogen; $R_2$=H, a halogen, a nitro group, a hydroxy group, or a methoxy group.

2. The compound of claim 1, wherein $R_1$=$R_2$=H.
3. The compound of claim 1, wherein $R_1$=H and $R_2$=Cl.
4. The compound of claim 1, wherein $R_1$=$R_2$=Cl.
5. The compound of claim 1, wherein $R_1$=H and $R_2$=Br.
6. The compound of claim 1, wherein $R_1$=$R_2$=Br.
7. The compound of claim 1, wherein $R_1$=H and $R_1$=a nitro group.
8. The compound of claim 1, wherein $R_1$=Cl and $R_2$=a nitro group.
9. The compound of claim 1, wherein $R_1$=Br and $R_2$=a nitro group.
10. The compound of claim 1, wherein $R_1$=H and $R_2$=a methoxy group.
11. The compound of claim 1, wherein $R_1$=H and $R_2$=a hydroxy group.
12. A pharmaceutical composition for treating tuberculosis, Herpes Simplex Virus, chlamydia or an immunodeficiency disease in an animal, wherein the pharmaceutical composition comprises a derivative of 5-oxo-5H-[1]-benzopyrano-[5,6-b]-4-oxo-4H-[1,2]-pyrimido-1,4,5,6-tetrahydro-1,3-thiazine(1) of the general formula:

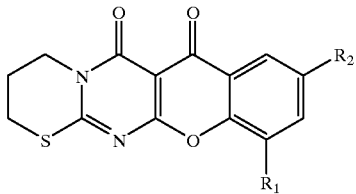

where $R_1$=H, or a halogen; $R_2$=H, a halogen, a nitro group, a hydroxy group, or a methoxy group; and a pharmaceutically acceptable carrier.

13. A method for treating tuberculosis, Herpes Simplex Virus, chlamydia, or an immunodeficiency disease in an animal, comprising administering to the animal a therapeutically effective amount of a derivative of 5-oxo-5H-[1]-benzopyrano-[5,6-b]-4-oxo-4H-[1,2]-pyrimido-1,4,5,6-tetrahydro-1,3-thiazine(1) of the general formula:

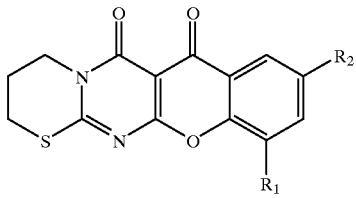

where $R_1$=H, or a halogen; $R_2$=H, a halogen, a nitro group, a hydroxy group, or a methoxy group.

* * * * *